United States Patent
Sun et al.

(10) Patent No.: US 7,022,714 B2
(45) Date of Patent: Apr. 4, 2006

(54) ARYL SUBSTITUTED BENZIMIDAZOLES AND THEIR USE AS SODIUM CHANNEL BLOCKERS

(75) Inventors: Qun Sun, Princeton, NJ (US); Xiaoming Zhou, Plainsboro, NJ (US); Donald J. Kyle, Newtown, PA (US)

(73) Assignee: Euro-Celtique S.A., Luxembourg (LU)

( * ) Notice: Subject to any disclaimer, the term of this patent is extended or adjusted under 35 U.S.C. 154(b) by 338 days.

(21) Appl. No.: 10/630,896

(22) Filed: Jul. 31, 2003

(65) Prior Publication Data

US 2004/0132777 A1 Jul. 8, 2004

Related U.S. Application Data

(60) Provisional application No. 60/399,458, filed on Jul. 31, 2002.

(51) Int. Cl.
*A61K 31/454* (2006.01)
*C07D 401/06* (2006.01)
*C07D 401/14* (2006.01)

(52) U.S. Cl. ............ 514/322; 546/199; 546/256; 514/338; 548/304.7; 548/306.1

(58) Field of Classification Search ............... 514/322, 514/338; 546/199, 256; 548/304.7, 306.1
See application file for complete search history.

(56) References Cited

U.S. PATENT DOCUMENTS

| | | | |
|---|---|---|---|
| 4,297,365 A * | 10/1981 | Rajappa et al. ............ 514/370 |
| 6,211,177 B1 | 4/2001 | Sperl et al. |
| 6,335,354 B1 | 1/2002 | Hogenkamp |
| 6,414,011 B1 | 7/2002 | Hogenkamp et al. |
| 2002/0006947 A1 | 1/2002 | Hogenkamp et al. |
| 2002/0022624 A1 | 2/2002 | Dinnell et al. |
| 2002/0040025 A1 | 4/2002 | Hogenkamp et al. |
| 2003/0055088 A1 | 3/2003 | Shao et al. |
| 2003/0069292 A1 | 4/2003 | Hogenkamp et al. |
| 2003/0073724 A1 | 4/2003 | Shao et al. |
| 2003/0109521 A1 | 6/2003 | Sun et al. |
| 2003/0236273 A1 | 12/2003 | Goehring et al. |
| 2004/0002523 A1 | 1/2004 | Hogenkamp et al. |

FOREIGN PATENT DOCUMENTS

| | | |
|---|---|---|
| JP | 2000-323278 | 11/2000 |
| WO | WO 98/08818 | 2/1999 |
| WO | WO 99/43672 | 2/1999 |
| WO | WO 01/21634 | 3/2001 |
| WO | WO 01/83472 | 11/2001 |

OTHER PUBLICATIONS

Laird, et al., "Analgesic Activity of a Novel Use-Dependent Sodium Channel Blocker, Crobenetine, in Mono-arthritic Rats," *Br. J. Pharmacol.* (2001) 134, 1742-1748.*
Bensimon, G., et al., "A Controlled Trail of Riluzole in Amyotrophic Lateral Sclerosis," *New Engl. J. Med.* 330: 585-591, Massachusetts Medical Society (1994).
Brown, C.M., et al., "Neuroprotective properties of lifarizine compared with those of other agents in a mouse model of focal cerebral ischaemia," *British J. Pharmacol.* 115:1425-1432, Stockton Press (1995).
Catterall, W.A., "Neurotoxins that Act on Voltage-Sensitive Channels in Excitable Membranes," *Ann. Rev. Pharmacol. Toxicol.* 20:15-43, Annual Reviews, Inc. (1980).
Catterall, W.A., "Structure and Function of Voltage-Sensitive Ion Channels," *Science* 242:50-61, American Association for the Advancement of Science (1988).
Catterall, W.A., "Common modes of drug action on NA+ channels: local anesthetics, antiarrhythmics and anticonvulsants," *Trends Pharmacol. Sci.* 8:57-65, Elsevier Science Publishers (1987).

(Continued)

*Primary Examiner*—Joseph K. McKane
*Assistant Examiner*—Andrew B. Freistein
(74) *Attorney, Agent, or Firm*—Sterne, Kessler, Goldstein & Fox P.L.L.C.

(57) ABSTRACT

This invention relates aryl substituted benzimidazoles of Formula I:

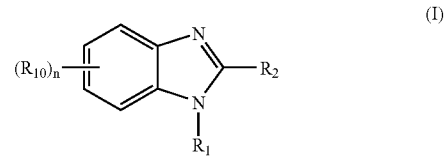

or a pharmaceutically acceptable salt, prodrug or solvate thereof, wherein $R_1$, $R_2$, $R_{10}$ and n are defined in the specification. The invention is also directed to the use of compounds of Formula I for the treatment of neuronal damage following global and focal ischemia, for the treatment or prevention of neurodegenerative conditions such as amyotrophic lateral sclerosis (ALS), and for the treatment, prevention or amelioration of both acute or chronic pain, as antitinnitus agents, as anticonvulsants, and as antimanic depressants, as local anesthetics, as antiarrhythmics and for the treatment or prevention of diabetic neuropathy.

43 Claims, No Drawings

OTHER PUBLICATIONS

Denicoff, K.D., et al., "Efficacy of Carbamazepine Compared With Other Agents: A Clinical Practice Survey," *J. Clin. Psychiatry* 55:70-76, Physicians Postgraduate Press (1994).

Donaldson, I., "Tegretol: A double blind trial in tinnitus," *J. Laryngol. Otol.* 95:947-951, Journal of Laryngology and Otology Ltd. (1981).

Graham, S.H., et al., "Neuroprotective Effects of a Use-Dependent Blocker of Voltage-Dependent Sodium Channels, BW619C89, in Rat Middle Cerebral Artery Occlusion," *J. Pharmacol. Exp. Ther.* 269:854-859, The American Society of Pharmacology and Experimental Therapeutics (1994).

Majumdar, B., et al., "An electrocochleographic study of the effects of lignocaine on patients with tinnitus," *Clin. Otolaryngol.* 8:175-180, Blackwell Scientific Publications (1983).

Mane, D.V., et al., "Synthesis and biological activity of some new 2-alkyl-1-(1'-dihydropyridylmethyl)benzimidazoles," *Indian J. Chem.* 34B:917-919, The Council of Scientific & Industrial Research (1995).

Moller, A.R., "Similarities Between Chronic Pain and Tinnitus," *Am. J. Otol.* 18:577-585, American Journal of Otology, Inc. (1997).

Simpson, J.J., and Davies, W.E., "Recent advances in the pharmacological treatment of tinnitus," *TIPS* 20:12-18, Elsevier Science (1999).

Srivastava, A.J., et al., "Synthesis and Antiviral Activity of Mannich Bases of 2-[(2-Oxo-4-Methyl-7-HydroxyQuinolinyl)-1-(4'-aryl)] Benzimidazole," *Indian Drugs* 28:75-77, Indian Drug Manufacturers' Association (1990).

Stys, P.K., et al., "Ionic Mechanisms of Anoxic Injury in Mammalian CNS White Matter: Role of $Na^+$ Channels and $Na^+$-$Ca^{2+}$ Exchanger," *J. Neurosci.* 12:430-439, Society for Neuroscience (1992).

Taylor, C.P., and Meldrum, B.S., "$Na^+$ channels as targets for neuroprotective drugs," *Trends Pharmacol. Sci.* 16:309-316, Elsevier Science Ltd. (1995).

Tonndorf, J., "The analogy between tinnitus and pain: A suggestion for a physiological basis of chronic tinnitus," *Hear. Res.* 28:271-275, Elsevier Science Publishers (1987).

English language abstract of EP 0 639 573 A1, Derwent World Patents Index (Dialog File 351), WPI Accession No. 10182147, (2003).

English language abstract of JP 2000323278, Derwent World Patents Index (Dialog File 351), WPI Accession No. 13736273, (2003).

International Search Report for PCT Application No. PCT/US 03/23828, mailed on January 20, 2004, European Patent Office, Netherlands.

Anger, T. et al., "Medicinal Chemistry of Neuronal Voltage-Gated Sodium Channel Blockers", *Journal of Medicinal Chemistry*, vol. 44, No. 2, pp. 115-137, published on web Jan. 11, 2001.

\* cited by examiner

ARYL SUBSTITUTED BENZIMIDAZOLES AND THEIR USE AS SODIUM CHANNEL BLOCKERS

This application claims the priority benefit under 35 U.S.C. § 119(e) of U.S. Provisional Application No. 60/399,458, filed Jul. 31, 2002, the entirety of which is incorporated by reference herein.

BACKGROUND OF THE INVENTION

1. Field of the Invention

This invention is in the field of medicinal chemistry. In particular, the invention relates to novel aryl substituted benzimidazoles, and the discovery that these compounds are blockers of sodium ($Na^+$) channels.

2. Related Art

Several classes of therapeutically useful drugs, including local anesthetics such as lidocaine and bupivacaine, antiarrhythmics such as propafenone and amioclarone, and anticonvulsants such as lamotrigine, phenyloin and carbamazepine, have been shown to share a common mechanism of action by blocking or modulating $Na^+$ channel activity (Catterall, W. A., Trends Pharmacol. Sci. 8:57–65 (1987)). Each of these agents is believed to act by interfering with the rapid influx of $Na^+$ ions.

Recently, other $Na^+$ channel blockers such as BW619C89 and lifarizine have been shown to be neuroprotective in animal models of global and focal ischemia and are presently in clinical trials (Graham et al., J. Pharmacol. Exp. Ther. 269:854–859 (1994); Brown et al., British J. Pharmacol. 115:1425–1432 (1995)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^+$ channel blockers prevent hypoxic damage to mammalian white matter (Stys et al., J. Neurosci. 12:430–439 (1992)). Thus, they can offer advantages for treating certain types of strokes or neuronal trauma where damage to white matter tracts is prominent.

Another example of clinical use of a $Na^+$ channel blocker is riluzole. This drug has been shown to prolong survival in a subset of patients with ALS (Bensimm et al., New Engl. J. Med. 330:585–591 (1994)) and has subsequently been approved by the FDA for the treatment of ALS. In addition to the above-mentioned clinical uses, carbamazepine, lidocaine and phenyloin are occasionally used to treat neuropathic pain, such as from trigeminal neurologia, diabetic neuropathy and other forms of nerve damage (Taylor and Meldrum, Trends Pharmacol. Sci. 16:309–316 (1995)), and carbamazepine and lamotrigine have been used for the treatment of manic depression (Denicott et al., J. Clin. Psychiatry 55:70–76 (1994)). Furthermore, based on a number of similarities between chronic pain and tinnitus, (Moller, A. R. Am. J. 0 to 1. 18:577–585 (1997); Tonndorf, J. Hear. Res. 28:271–275 (1987)) it has been proposed that tinnitus should be viewed as a form of chronic pain sensation (Simpson, J. J. and Davies, E. W. Tips. 20:12–18 (1999)). Indeed, lignocaine and carbamazepine have been shown to be efficacious in treating tinnitus (Majumdar, B. et al. Clin. Otolaryngol. 8:175–180 (1983); Donaldson, I. Laryngol. Otol. 95:947–951 (1981)).

It has been established that there are at least five to six sites on the voltage-sensitive $Na^+$ channels which bind neurotoxins specifically (Catterall, W. A., Science 242: 50–61 (1988)). Studies have further revealed that therapeutic antiarrhythmics, anticonvulsants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., Ann. Rev. Pharmacol. Toxicol. 10:15–43 (1980)).

A need exists in the art for novel compounds that are potent blockers of sodium channels, and are therefore useful for treating a variety of central nervous system conditions, including pain.

SUMMARY OF THE INVENTION

One aspect of the present invention is directed to novel aryl substituted benzimidazoles of Formula I.

The present invention is also related to the discovery that aryl substituted benzimidazoles of Formula I act as blockers of sodium ($Na^+$) channels.

Another aspect of the present invention is directed to the use of novel compounds of Formula I as blockers of sodium channels.

The invention is also related with treating a disorder responsive to the blockade of sodium channels in a mammal suffering from excess activity of said channels by administering an effective amount of a compound of Formula I as described herein.

A further aspect of the present invention is to provide a method for treating, preventing or ameliorating neuronal loss following global and focal ischemia; treating, preventing or ameliorating pain including acute and chronic pain, and neuropathic pain; treating, preventing or ameliorating convulsion and neurodegenerative conditions; treating, preventing or ameliorating manic depression; using as local anesthetics and anti-arrhythmics, and treating tinnitus by administering a compound of Formula I to a mammal in need of such treatment or use.

Also, an aspect of the present invention is to provide a pharmaceutical composition useful for treating disorders responsive to the blockade of sodium ion channels, containing an effective amount of a compound of Formula I in a mixture with one or more pharmaceutically acceptable carriers or diluents.

Additional embodiments and advantages of the invention will be set forth in part in the description that follows, and in part will be obvious from the description, or can be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

Novel compounds of the present invention are aryl substituted benzimidazoles of Formula I:

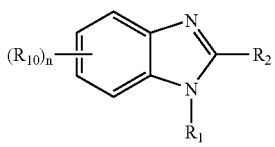

or a pharmaceutically acceptable salt, or solvate thereof, wherein:

$R_1$ is selected from the group consisting of:

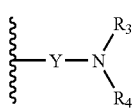

where
Y is an optionally substituted $C_{2-6}$ alkylene, and
$R_3$ and $R_4$ are the same or different and are selected from hydrogen, alkyl, or aryl, or $R_3$ and $R_4$ together with the nitrogen to which they are attached form a ring having 4 or 5 carbon atoms, which ring optionally contains 1 or 2 additional heteroatoms independently selected from oxygen and $NR_5$, where $R_5$ is hydrogen or alkyl, or said ring is optionally substituted with an alkyl or aryl moiety;
(ii) pyridylalkyl; and
(iii) piperidin-4-ylalkyl, optionally substituted by alkyl, aryl or aralkyl;

$R_2$ is selected from the group consisting of:
(i) optionally substituted phenoxyphenyl;
(ii) optionally substituted benzyloxyphenyl;
(iii) optionally substituted phenylthiophenyl;
(iv) optionally substituted benzylthiophenyl;
(v) optionally substituted phenylaminophenyl;
(vi) optionally substituted benzylaminophenyl;

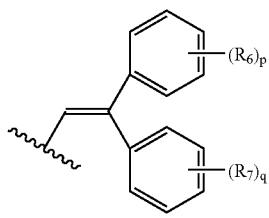

wherein $R_6$ and $R_7$ are independently halogen, alkyl, alkoxy, or haloalkyl; and p and q are integers from 0 to 4;

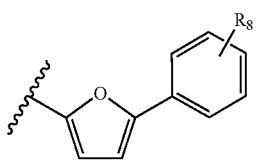

wherein $R_8$ is hydrogen, halogen, alkyl or alkoxy;

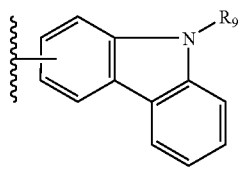

wherein $R_9$ is hydrogen or alkyl; and
(x) naphthyl;
$R_{10}$ is selected from halogen, hydroxy, alkyl, alkoxy and alkoxyalkyl, wherein any alkyl moiety of $R_{10}$ can be optionally substituted by one or more of halogen or hydroxy; and
n is an integer from 0 to 4, where when n is 0, $R_{10}$ is absent and the benzene ring of the benzimidazole compound has four hydrogen atoms attached thereto, and when $R_{10}$ is present, $R_{10}$ replaces one or more of the available hydrogen atoms on the benzene ring of the benzimidazole compound.

Preferred compounds of Formula I are those wherein $R_2$ is phenoxyphenyl or benzyloxyphenyl, wherein the phenyl group of the phenoxy or benzyloxy moiety is optionally substituted with alkyl, alkoxy, halogen or haloalkyl. Preferred substituents include one to three, preferably one or two, substituents independently selected from the group consisting of $C_{1-4}$ alkyl, $C_{1-4}$ alkoxy, halogen, and $C_{1-4}$ haloalkyl. Suitable values of $R_2$ in this embodiment of the invention include (3-phenoxy)phenyl, (4-phenoxy)phenyl, (3-benzyloxy)phenyl, or (4-benzyloxy)phenyl, any of which is optionally substituted by one, two or three groups independently selected from the group consisting of fluoro, chloro, bromo, methyl, ethyl, propyl, isopropyl, methoxy, ethoxy, fluoromethyl, and trifluormethyl.

Preferred compounds of Formula I are those wherein $R_2$ is optionally substituted phenoxyphenyl or optionally substituted benzyloxyphenyl; $R_3$ and $R_4$ together with the nitrogen to which they are attached form a piperidinyl, morpholinyl or pyrrolidinyl group; and Y is an optionally substituted $C_{2-6}$ alkylene chain.

Preferred compounds of Formula I are also those wherein $R_2$ is optionally substituted phenoxyphenyl or optionally substituted benzyloxyphenyl; and $R_3$ and $R_4$ are independently hydrogen, alkyl or aryl; and Y is an optionally substituted $C_{2-6}$ alkylene chain.

Preferred compounds are those of Formula I wherein $R_2$ is

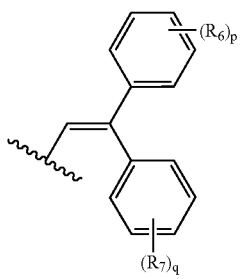

where $R_6$ and $R_7$ are independently alkyl, alkoxy, halogen, or haloalkyl, and p and q are independently 0–4, preferably 0, 1 or 2. When $R_6$ and/or $R_7$ is present, these groups substitute for hydrogen atoms at any available position on the phenyl to which they are attached. Preferably, $R_6$ and $R_7$ are independently $C_{1-4}$ alkyl, $C_{1-4}$ alkoxy, halogen, or $C_{1-4}$ haloalkyl. Useful values of $R_6$ and $R_7$ include fluoro, chloro, bromo, methyl, ethyl, propyl, isopropyl, methoxy, ethoxy, fluoromethyl, and trifluormethyl.

Additionally, preferred compounds are those of Formula I wherein $R_2$ is

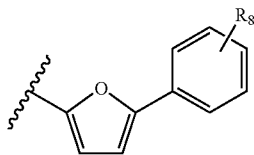

where $R_8$ is as defined above, and is preferably hydrogen or $C_{1-4}$ alkyl, such as methyl, ethyl, propyl and isopropyl. $R_8$ replaces a hydrogen atom at any available position on the phenyl ring.

Additionally, preferred compounds are those of Formula I wherein $R_2$ is

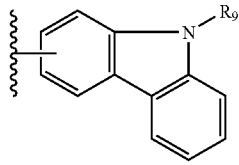

where $R_9$ is as defined above, and is preferably hydrogen or $C_{1-4}$ alkyl, such as methyl, ethyl, propyl and isopropyl.

Preferred compounds also are those of Formula I wherein $R_2$ is naphthalyl.

Further, additionally preferred compounds of Formula I are those wherein when $R_2$ is phenoxyphenyl or the benzyloxyphenyl, $R_2$ is attached to the benzimidazole at the 3- or 4-position of the phenyl component of the phenoxyphenyl or the benzyloxyphenyl.

Preferred compounds also are those of Formula I wherein $R_1$ is

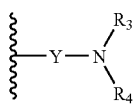

where $R_3$ and $R_4$ are defined above.

Still, additionally preferred compounds of Formula I are those wherein $R_1$ is $—Y—NR_3R_4$, where Y is an optionally substituted $C_{2-6}$ alkylene and $R_3$ and $R_4$ together with the nitrogen to which they are attached form a piperidinyl, morpholinyl or pyrrolidinyl group.

Other preferred compounds of Formula I are those wherein Y is an optionally substituted $C_{2-6}$ alkylene; and $R_3$ and $R_4$ are the same or different and are selected from hydrogen, $C_{1-6}$ alkyl, and $C_{6-10}$ aryl.

For purposes of the present invention, the term "alkylene" has the meaning $—(CH_2)_m—$, where m is an integer of from 1–6, preferably 2–4. Suitable alkylene chains include but are not limited to methylene, ethylene, propylene, butylene, pentylene and hexylene. The alkylene chain can also be optionally substituted.

Additionally preferred compounds of Formula I are those wherein $R_1$ is pyridylalkyl.

Preferred compounds of Formula I are also those wherein $R_1$ is piperidin-4-ylalkyl, optionally substituted by $C_{1-6}$ alkyl, $C_{6-10}$ aryl or $C_{6-10}$ ar($C_{1-6}$)alkyl.

The term "alkyl," when not further defined, means a linear or branched $C_{1-10}$ carbon chain, preferably a $C_{1-6}$ carbon chain. Suitable alkyl groups include, but are not limited to, methyl, ethyl, propyl, isopropyl, butyl, isobutyl, sec-butyl, tert-butyl, 3-pentyl, hexyl and octyl groups.

The term "optionally substituted," when not further defined, means replacement of one or more carbon-attached hydrogens with halogen, halo($C_{1-6}$)alkyl, aryl, heterocycle, cycloalkyl, $C_{1-6}$ alkyl, $C_{2-6}$ alkenyl, $C_{2-6}$ alkynyl, aryl($C_{1-6}$) alkyl, aryl($C_{2-6}$)alkenyl, aryl($C_{2-6}$)alkynyl, cycloalkyl($C_{1-6}$) alkyl, heterocyclo($C_{1-6}$ alkyl), hydroxy($C_{1-6}$)alkyl, amino ($C_{1-6}$)alkyl, carboxy($C_{1-6}$) alkyl, alkyloxy($C_{1-6}$)alkyl, nitro, amino, ureido, cyano, acylamino, hydroxy, thiol, acyloxy, azido, alkyloxy, carboxy, aminocarbonyl, and $C_{1-6}$ alkylthiol. Preferred "optionally substituted alkyl" include aryl and halogen.

The term "optionally substituted alkylene chain," when not further defined, means replacement of an alkylene hydrogen with one or more alkyl groups, aryl groups and halogen atoms. Preferred "optionally substituted alkylene chain" include alkyl groups and halogen atoms, preferably alkyl groups.

The term "aryl," when not further defined, means a $C_{6-14}$ mono- or polycyclic aromatic ring system. Suitable carbocyclic aryl groups include, but are not limited to, phenyl, naphthyl, phenanthryl, anthracyl, indenyl, azulenyl, biphenyl, biphenylenyl and fluorenyl groups. Particularly preferred carbocyclic aryl groups are phenyl and naphthyl.

Exemplary compounds that can be employed in this method of invention include, without limitation:
3-(2-piperidinylethyl)-2-(4-phenoxyphenyl)benzimidazole;
3-(2-piperidinylethyl)-2-(3-(4-tert-butylphenoxy)phenyl) benzimidazole;
3-(2-piperidinylethyl)-2-(3-(3,4-dichlorophenoxy)phenyl) benzimidazole;
3-(2-piperidinylethyl)-2-(2,2-diphenylethenyl)benzimidazole;
3-(2-piperidinylethyl)-2-(3-phenoxyphenyl)benzimidazole;
3-(2-piperidinylethyl)-2-(3-(3-trifluoromethylphenoxy)phenyl)benzimidazole;
3-(2-piperidinylethyl)-2-(N-ethyl-3-carbazolyl)benzimidazole;
3-(2-piperidinylethyl)-2-(3-benzyloxyphenyl)benzimidazole; and
3-(2-piperidinylethyl)-2-(4-(4-fluorophenoxy)phenyl)benzimidazole;

as well as pharmaceutically acceptable salts thereof.
Particularly preferred compounds are selected from:
3-(2-piperidinylethyl)-2-(4-phenoxyphenyl)benzimidazole;
3-(2-piperidinylethyl)-2-(3-(4-tert-butylphenoxy)phenyl) benzimidazole;
3-(2-piperidinylethyl)-2-(3-(3,4-dichlorophenoxy)phenyl) benzimidazole;
3-(2-piperidinylethyl)-2-(2,2-diphenylethenyl)benzimidazole;
3-(2-piperidinylethyl)-2-(3-phenoxyphenyl)benzimidazole;
3-(2-piperidinylethyl)-2-(3-(3-trifluoromethylphenoxy)phenyl)benzimidazole;

3-(2-piperidinylethyl)-2-(3-benzyloxyphenyl)benzimidazole; and 3-(2-piperidinylethyl)-2-(4-(4-fluorophenoxy)phenyl)benzimidazole;

as well as pharmaceutically acceptable salts thereof.

The invention disclosed herein is meant to encompass all pharmaceutically acceptable salts thereof of the disclosed compounds. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

The invention disclosed herein is also meant to encompass prodrugs of the disclosed compounds. Prodrugs are considered to be any covalently bonded carrier which releases the active parent drug in vivo.

The invention disclosed herein is also meant to encompass the in vivo metabolic products of the disclosed compounds. Such products can result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Some of the compounds disclosed herein can contain one or more asymmetric centers and can thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

The benzimidazoles of Formula I can be prepared using methods known to those skilled in the art. Specifically, the benzimidazoles of the present invention are generally obtained from a method comprising:

(a) reacting a primary amine with 2-fluoro-1-nitrobenzene to produce an amine substituted nitrobenzene;

(b) reducing said amine substituted nitrobenzene obtained in (a) in the presence of hydrogen and a catalyst to produce an amine substituted aniline; and (c) reacting said amine substituted aniline obtained in step (b), with an aldehyde to produce a substituted benzimidazole of Formula For this method, the primary amine in step (a) is selected from the groups consisting of:

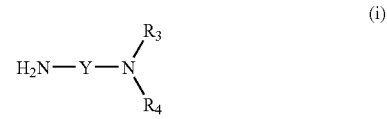

(i)

wherein

Y is an optionally substituted $C_{2-6}$ alkylene; and $R_3$ and $R_4$ are the same or different and are selected from hydrogen, alkyl, or aryl, or $R_3$ and $R_4$ together with the nitrogen to which they are attached form a ring having 4 or 5 carbon atoms, which ring optionally contains 1 or 2 additional heteroatoms independently selected from oxygen and $NR_5$, where $R_5$ is hydrogen or alkyl, or said ring is optionally substituted with an alkyl or aryl moiety;

(ii) pyridylalkyl amine; and (iii) an optionally substituted piperidin-4-ylalkyl amine, wherein optional substituents are selected from the group consisting of alkyl, aryl or aralkyl. Preferred values of Y, $R_3$ and $R_4$ are as described above.

Additionally, for this method, the aldehyde in (c) has the formula:

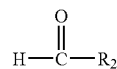

wherein $R_2$ is as defined above.

The reaction time for steps (a) and (b) above, is generally between about 14 to about 17 hours and results in yields of greater than 90%. The reaction time for step (c) is about 45 to about 50 hours and results in product yields of from about 60 to about 95%.

The reduction of step (b) is generally carried out at a pressure of about 2 to about 4 atms, preferably about 3 atms.

The general method of making benzimidazoles of the present invention is shown in the following reaction scheme.

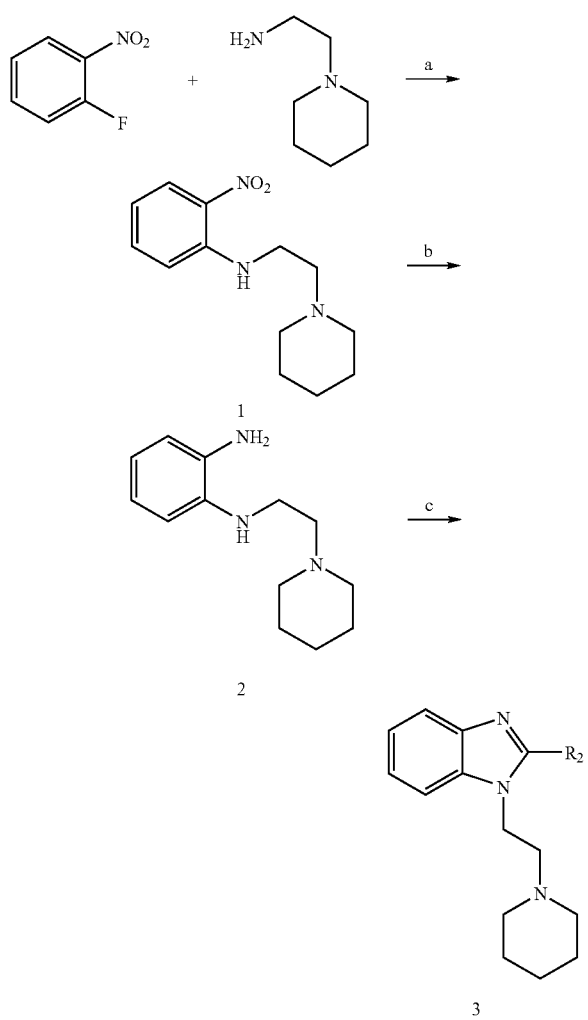

Reagents/Reaction Times: (a) 5% DIEA/DMF, 14–17 hrs; (b) Pd/C, H$_2$, 3 atm, MeOH, 16 hrs; (c) aldehyde, PhNO$_2$, 100° C., 45–50 hrs.

The invention is also directed to a method for treating disorders responsive to the blockade of sodium channels in mammals suffering therefrom. The benzimidazole compounds of the invention can be used to treat humans or companion animals, such as dogs and cats. Particular preferred embodiments of the benzimidazoles of the invention for use in treating such disorders are represented as previously defined for Formula I.

The compounds of the present invention are assessed by electrophysiological assays in dissociated hippocampal neurons for sodium channel blocker activity. These compounds also can be assayed for binding to the neuronal voltage-dependent sodium channel using rat forebrain membranes and [$^3$H]BTX-B.

Sodium channels are large transmembrane proteins that are expressed in various tissues. They are voltage sensitive channels and are responsible for the rapid increase of Na$^+$ permeability in response to depolarization associated with the action potential in many excitable cells including muscle, nerve and cardiac cells.

One aspect of the present invention is the discovery of the mechanism of action of the compounds herein described as specific Na$^+$ channel blockers. Based upon the discovery of this mechanism, these compounds are contemplated to be useful in treating or preventing neuronal loss due to focal or global ischemia, and in treating or preventing neurodegenerative disorders including ALS, depression, and epilepsy. They are also expected to be effective in treating, preventing or ameliorating neuropathic pain, surgical pain, chronic pain and tinnitus. The compounds are also expected to be useful as antiarrhythmics, anesthetics and antimanic depressants.

The present invention is directed to compounds of Formula I that are blockers of voltage-sensitive sodium channels. According to the present invention, those compounds having preferred sodium channel blocking properties exhibit an IC$_{50}$ of about 100 µM or less in the electrophysiological assay described herein. Preferably, the compounds of the present invention exhibit an IC$_{50}$ of 10 µM or less. Most preferably, the compounds of the present invention exhibit an IC$_{50}$ of about 1.0 µM or less. Compounds of the present invention can be tested for their Na$^+$ channel blocking activity by the following binding and electrophysiological assays.

In Vitro Binding Assay:

The ability of compounds of the present invention to modulate either site 1 or site 2 of the Na$^+$ channel was determined following the procedures fully described in Yasushi, J. Biol. Chem. 261:6149–6152 (1986) and Creveling, Mol. Pharmacol. 23:350–358 (1983), respectively. Rat forebrain membranes are used as sources of Na$^+$ channel proteins. The binding assays are conducted in 130 µM choline chloride at 37° C. for 60-minute incubation with [$^3$H] saxitoxin and [$^3$H] batrachotoxin as radioligands for site 1 and site 2, respectively.

In Vivo Pharmacology:

The compounds of the present invention can be tested for in vivo anticonvulsant activity after i.v., p.o. or i.p. injection using a number of anticonvulsant tests in mice, including the maximum electroshock seizure test (MES). Maximum electroshock seizures are induced in male NSA mice weighing between 15–20 g and male Sprague-Dawley rats weighing between 200–225 g by application of current (50 mA, 60 pulses/sec, 0.8 msec pulse width, 1 sec duration, D.C., mice; 99 mA, 125 pulses/sec, 0.8 msec pulse width, 2 sec duration, D.C., rats) using a Ugo Basile ECT device (Model 7801). Mice are restrained by gripping the loose skin on their dorsal surface and saline-coated corneal electrodes were held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results are treated in a quantal manner.

The compounds can be tested for their antinociceptive activity in the formalin model as described in Hunskaar, S., O. B. Fasmer, and K. Hole, J. Neurosci. Methods 14: 69–76 (1985). Male Swiss Webster NIH mice (20–30 g; Harlan, San Diego, Calif.) are used in all experiments. Food is withdrawn on the day of experiment. Mice are placed in Plexiglass jars for at least 1 hour to accommodate to the environment. Following the accommodation period mice are weighed and given either the compound of interest administered i.p. or p.o., or the appropriate volume of vehicle (10% Tween-80). Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5 minute intervals for 1 hour after the formalin injection. All experiments are done in a blinded manner during the light cycle. The early phase of the formalin response is measured as licking/biting between 0–5 minutes, and the late phase is measured from 15–50 minutes. Differences between vehicle and drug treated groups are analyzed by one-way analysis of variance (ANOVA). A P value <0.05 is considered significant. Activity in blocking the acute and second phase of formalin-induced paw-licking activity is indicative that compounds are considered to be efficacious for acute and chronic pain.

The compounds can be tested for their potential for the treatment of chronic pain (antiallodynic and antihyperalgesic activities) in the Chung model of peripheral neuropathy. Male Sprague-Dawley rats weighing between 200–225 g are anesthetized with halothane (1–3% in a mixture of 70% air and 30% oxygen) and their body temperature is controlled during anesthesia through use of a homeothermic blanket. A 2-cm dorsal midline incision is then made at the L5 and L6 level and the para-vertibral muscle groups retracted bilaterally. L5 and L6 spinal nerves are then be exposed, isolated, and tightly ligated with 6–0 silk suture. A sham operation is performed exposing the contralateral L5 and L6 spinal nerves as a negative control.

Tactile Allodynia: Rats are transferred to an elevated testing cage with a wire mesh floor and allowed to acclimate for five to ten minutes. A series of Semmes-Weinstein monofilaments are applied to the plantar surface of the hindpaw to determine the animal's withdrawal threshold. The first filament used possesses a buckling weight of 9.1 g (0.96 log value) and is applied up to five times to see if it elicited a withdrawal response. If the animal has a withdrawal response then the next lightest filament in the series is applied up to five times to determine if it can elicit a response. This procedure is repeated with subsequent less filaments until there is no response and the lightest filament that elicits a response is recorded. If the animal does not have a withdrawal response from the initial 9.1 g filament then subsequent filaments of increased weight are applied until a filament elicits a response and this filament is then recorded. For each animal, three measurements are made at every time point to produce an average withdrawal threshold determination. Tests are performed prior to and at 1, 2, 4 and 24 hours post drug administration. Tactile allodynia and mechanical hyperalgesia tests were conducted concurrently.

Mechanical Hyperalgesia: Rats are transferred to an elevated testing cage with a wire mesh floor and allowed to acclimate for five to ten minutes. A slightly blunted needle is touched to the plantar surface of the hindpaw causing a dimpling of the skin without penetrating the skin. Administration of the needle to control paws typically produces a quick flinching reaction, too short to be timed with a stopwatch and arbitrarily gives a withdrawal time of 0.5 second. The operated side paw of neuropathic animals exhibits an exaggerated withdrawal response to the blunted needle. A maximum withdrawal time of ten seconds is used as a cutoff time. Withdrawal times for both paws of the animals are measured three times at each time point with a five-minute recovery period between applications. The three measures are used to generate an average withdrawal time for each time point. Tactile allodynia and mechanical hyperalgesia tests are conducted concurrently.

The compounds can be tested for their neuroprotective activity after focal and global ischemia produced in rats or gerbils according to the procedures described in Buchan et al. (Stroke, Suppl. 148–152 (1993)) and Sheardown et al. (Eur. J. Pharmacol. 236:347–353 (1993)) and Graham et al. (J. Pharmacol. Exp. Therap. 276:1–4 (1996)).

The compounds can be tested for their neuroprotective activity after traumatic spinal cord injury according to the procedures described in Wrathall et al. (Exp. Neurology 137:119–126 (1996)) and Iwasaki et al. (J. Neuro Sci. 134:21–25 (1995)).

Electrophysiological Assay:

An electrophysiological assay was used to measure potencies of compounds of the present invention rBIIa/beta 1 sodium channels expressed in *Xenopus* oocytes.

Preparation of cDNA encoding cloned rat brain type IIa (rBIIa) and beta 1 ($\beta$1): cDNA clones encoding the rat brain beta 1 subunit are cloned in house using standard methods, and mRNA are prepared by standard methods. mRNA encoding rBIIa is provided by Dr. A. Golden (UC Irvine). The mRNAs are diluted and stored at −80° C. in 1 μL aliquots until injection.

Preparation of oocytes: Mature female *Xenopus laevis* are anaesthetized (20–40 min) using 0.15% 3-aminobenzoic acid ethyl ester (MS-222) following established procedures (Woodward, R. M., et al., Mol. Pharmacol. 41:89–103 (1992)).

Two to six ovarian lobes are surgically removed. Oocytes at developmental stages V–VI are dissected from the ovary, wherein the oocytes are still surrounded by enveloping ovarian tissues. Oocytes are defolliculated on the day of surgery by treatment with collagenase (0.5 mg/mL Sigma Type I, or Boehringer Mannheim Type A, for 0.5–1 hr). Treated oocytes are vortexed to dislodge epithelia, washed repeatedly and stored in Barth's medium containing 88 mM NaCl, 1 mM KCl, 0.41 mM $CaCl_2$, 0.33 mM $Ca(NO_3)_2$, 0.82 mM $MgSO_4$, 2.4 mM $NaHCO_3$, 5 mM HEPES, pH 7.4 adjusted with 0.1 mg/mL gentamycin sulphate.

Micro-injection of oocytes: Defolliculated oocytes are micro-injected using a Nanoject injection system (Drummond Scientific Co., Broomall, Pa.). Injection pipettes are beveled to minimize clogging. Tip diameter of injection pipettes is 15–35 μm. Oocytes are microinjected with approximately 50 nL 1:10 ratio mixtures of cRNAs for rBIIa and beta 1 respectively.

Electrophysiology: Membrane current responses are recorded in frog Ringer solution containing 115 mM NaCl, 2 mM KCl, 1.8 mM $CaCl_2$, 5 mM HEPES, pH 7.4. Electrical recordings are made using a conventional two-electrode voltage clamp (Dagan TEV-200) over periods ranging between 1–7 days following injection. The recording chamber is a simple gravity fed flow-through chamber (volume 100–500 mL depending on adjustment of aspirator). Oocytes are placed in the recording chamber, impaled with electrodes and continuously perfused (5–15 mL $min^{-1}$) with frog Ringer's solution. The tested compounds are applied by bath perfusion.

Voltage protocols for evoking sodium channel currents: The standard holding potential for whole oocyte clamp is −120 mV. Standard current-voltage relationships are elicited by 40 ms depolarizing steps starting from −60 mV to +50 mV in 10 mV increments. Peak currents are measured as the maximum negative current after depolarizing voltage steps. The voltage from maximum current response is noted and used for the next voltage protocol.

The purpose is to find compounds that are state dependent modifiers of neuronal sodium channels. Preferably, the compounds have a low affinity for the rested/closed state of the channel, but a high affinity for the inactivated state. The following voltage protocol is used to measure a compounds affinity for the inactivated state. Oocytes are held at a holding potential of −120 mV. At this membrane voltage, nearly all of the channels are in the closed state. Then a 4 second depolarization is made to the voltage where the maximum current is elicited. At the end of this depolarization, nearly all the channels are in the inactivated state. A 10 ms hyperpolarizing step is then made in order to remove some channels from the inactivated state. A final depolarizing test pulse is used to assay the sodium current after this prolonged depolarization (see analysis below). Sodium currents are measured at this test pulse before and after the application of the tested compound. Data is acquired using PCLAMP 8.0 software and analyzed with CLAMPFIT software (Axon instruments).

Data analysis: Apparent inhibition constants ($K_i$ values) for antagonists are determined from single point inhibition data using the following equation (a generalized form of the Cheng-Prusoff equation) (Leff, P. and I. G. Dougall, TiPS 14:110–112 (1993)).

$$K_i = (FR/1-FR)*[\text{drug}] \quad \text{Eq.1}$$

Where FR is the fractional response and is defined as sodium current elicited from the final depolarizing test pulse prior to application of the drug divided by the sodium current measured in the presence of the drug. [drug] is the concentration of the drug used.

Drugs: Drugs are initially made up at concentrations of 2–10 mM in DMSO. Dilutions are then made to generate a series of DMSO stocks over the range 0.3 µM to 10 mM—depending upon the potency of the compound. Working solutions are made by 1000–3000 fold dilution of stocks into Ringer. At these dilutions DMSO alone has little or no measurable effects on membrane current responses. DMSO stocks of drugs are stored in the dark at 4° C. Ringer solutions of drugs are made up fresh each day of use.

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds can be administered to mammals, e.g. humans, orally at a dose of 0.0025 to 50 mg/kg, or an equivalent amount of the pharmaceutically acceptable salt thereof, per day of the body weight of the mammal being treated for epilepsy, neurodegenerative diseases, anesthetic, arrhythmia, manic depression, and chronic pain. For intramuscular injection, the dose is generally about one-half of the oral dose.

In the method of treatment or prevention of neuronal loss in global and focal ischemia, brain and spinal cord trauma, hypoxia, hypoglycemia, status epilepsy and surgery, the compound can be administered by intravenous injection at a dose of about 0.025 to about 10 mg/kg.

The unit oral dose can comprise from about 0.01 to about 50 mg, preferably about 0.1 to about 10 mg of the compound. The unit dose can be administered one or more times daily as one or more tablets each containing from about 0.1 to about 10, conveniently about 0.25 to 50 mg of the compound or its solvates.

In addition to administering the compound as a raw chemical, the compounds of the invention can be administered as part of a pharmaceutical preparation containing suitable pharmaceutically acceptable carriers comprising excipients and auxiliaries which facilitate processing of the compounds into preparations that can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular benzimidazoles of the present invention, with a solution of a pharmaceutically acceptable non-toxic acid such as, but not limited to: acetic acid, benzoic acid, carbonic acid, citric acid, dichloroacetic acid, dodecylsulfonic acid, 2-ethylsuccinic acid, fumaric acid, glubionic acid, gluconic acid, hydrobromic acid, hydrochloric acid, 3-hydroxynaphthoic acid, isethionic acid, lactic acid, lactobionic acid, levulinic acid, maleic acid, malic acid, malonic acid, methanesulfic acid, methanesulfonic acid, nitric acid, oxalic acid, phosphoric acid, propionic acid, sulfuric acid, sulfamic acid, saccharic acid, succinic acid, tartaric acid, and the like. Basic amine salts are formed by mixing a solution of the benzimidazole compounds of the present invention with a solution of a pharmaceutically acceptable non-toxic acid such as those listed above, and preferably, hydrochloric acid or carbonic acid.

The pharmaceutical compositions of the invention can be administered to any animal that can experience the beneficial effects of the compounds of the invention. Foremost among such animals are mammals, e.g., humans and companion animals such as, dogs and cats, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, or buccal routes. Alternatively, or concurrently, administration can be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions can be used, which can optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers can be added.

Possible pharmaceutical preparations, which can be used rectally, include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances which increase the viscosity of the suspension, and include, for example, sodium carboxymethyl cellulose, sorbitol, and/or dextran. Optionally, the suspension can also contain stabilizers.

The following examples are illustrative, but not limiting, of the method and compositions of the present invention.

Other suitable modifications and adaptations of the variety of conditions and parameters normally encountered in clinical therapy and which are obvious to those skilled in the art are within the spirit and scope of the invention.

EXAMPLE 1

2-Nitrophenyl-aminoethyl Piperidine (1)

To a solution of 1-(2-aminoethyl)piperidine (10.0 g, 78.0 mmol) and 2-fluoro-1-nitrobenzene (22.0 g, 156.0 mmol) in DMF (250 mL) was added diisopropylethylamine (12.5 mL) and the mixture was stirred at room temperature for 15 hours. The reaction mixture was poured into a mixture of $CHCl_3$ and water. The water layer was extracted with $CHCl_3$ and the combined organic layers were washed with water and brine, dried ($Na_2SO_4$), and evaporated, and the residue was purified by silica gel column chromatography to give 1 (17.6 g, 91%) as a yellowish solid.

N-(2-piperidin-1-yl-ethyl)-benzene-1,2-diamine (2)

To a solution of 1 (1.30 g, 5.21 mmol) in MeOH (75 mL) was added 10% Pd—C (0.130 g). The mixture was agitated under a hydrogen atmosphere at room temperature and a pressure of 3 atm, for 16 hours. The catalyst was filtered off and washed with MeOH. The eluent was concentrated in vacuo to give the crude product 2 (1.20 g) with >95% purity as a slight yellowish oil. The crude product 2 was used for the next step without further purification.

2-Substitued-1-(2-piperidin-1-yl-ethyl)-1H-benzoimidazole (3)

To a solution of the above crude 2 (0.150 g, 0.685 mmol) in nitrobenzene (2.0 mL) was added an appropriate aldehyde (1.370 mmol) and the mixture was agitated at 100° C. for 48 hours. After cooling to room temperature, the mixture was directly poured onto a silica gel column and purified with a gradient elution (100% hexane, 90% hexane/ethyl acetate to 100% ethyl acetate) to give 3 in 60–85% yield as a yellowish solid. The recovered product was purified by column chromatography.

TABLE 1

STRUCTURES OF REPRESENTATIVE BENZIMIDAZOLE COMPOUNDS OF THE INVENTION

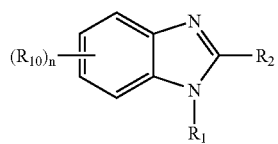

| Compound | n | $R_1$ | $R_2$ |
|---|---|---|---|
| 3a | 0 | (piperidin-1-yl-ethyl) | (4-phenoxyphenyl) |

TABLE 1-continued

STRUCTURES OF REPRESENTATIVE BENZIMIDAZOLE
COMPOUNDS OF THE INVENTION

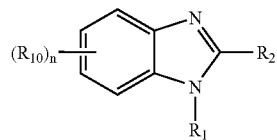

| Compound | n | R₁ | R₂ |
| --- | --- | --- | --- |
| 3b | 0 | piperidinyl-propyl | 3-(4-tert-butylphenoxy)phenyl |
| 3c | 0 | piperidinyl-propyl | 3-(3,4-dichlorophenoxy)phenyl |
| 3d | 0 | piperidinyl-propyl | 2,2-diphenylvinyl |
| 3e | 0 | piperidinyl-propyl | 3-phenoxyphenyl |
| 3f | 0 | piperidinyl-propyl | 3-[3-(trifluoromethyl)phenoxy]phenyl |
| 3g | 0 | piperidinyl-propyl | 9-ethyl-9H-carbazol-3-yl |

TABLE 1-continued

STRUCTURES OF REPRESENTATIVE BENZIMIDAZOLE COMPOUNDS OF THE INVENTION

| Compound | n | $R_1$ | $R_2$ |
|---|---|---|---|
| 3h | 0 | piperidinyl-ethyl | 3-(benzyloxy)phenyl |
| 3i | 0 | piperidinyl-ethyl | 4-(4-fluorophenoxy)phenyl |

Physical data for each of compounds 1–3a–i appear in Table 2 below.

TABLE 2

PROTON NMR DATA AND MASS SPECTROSCOPY DATA FOR BENZIMIDAZOLE COMPOUNDS OF THE INVENTION

| Compound | $^1$H NMR(400 MHz, CDCl$_3$); MS (ESI) m/z |
|---|---|
| 1 | δ 8.45(br, 1H), 8.18(d, 1H, J=8.3Hz), 7.43(d 1H, J=7.0, 8.3Hz), 6.86(d, 1H, J=8.3Hz), 6.63(dd, 1H, J=7.0, 8.3Hz), 3.43(m, 2H), 2.71(m, 2H), 2.51(m, 4H), 1.66(m, 4H), 1.48(m, 2H); MS(ESI) m/z for $C_{13}H_{19}N_3O_2$ (MH$^+$): 250.2. |
| 2 | δ 6.76(m, 1H), 6.65(m, 3H), 6.59(d, 1H, J=7.5 Hz), 6.51(m, 2H), 6.26(d, 1H, J=7.5Hz), 3.29(m, 2H), 2.88(m, 2H), 2.61(m, 4H), 1.69(m, 4H), 1.49(m, 2H); MS(ESI) m/z for $C_{13}H_{21}N_3$ (MH$^+$): 220.2. |
| 3a | δ 7.83(m, 1H), 7.80(d, 2H, J=8.7Hz), 7.46(m, 1H), 7.41(m, 2H), 7.32(m, 2H), 7.21 (m, 1H), 7.15(m, 2H), 7.10(m, 2H), 4.38(t, 2H, J=7.2Hz), 2.76(t, 2H, J=7.2Hz), 2.40(br, 4H), 1.55(m, 4H), 1.44(m, 2H); MS(ESI) m/z for $C_{26}H_{27}N_3O$(MH$^+$): 398.2. |
| 3b | δ 7.83(m, 1H), 7.52(m, 2H), 7.46(m, 2H), 7.38(d, 2H, J=8.7Hz), 7.32(m, 2H), 7.18 (m, 1H), 7.01(d, 2H, J=8.7Hz), 4.35(t, 2H, J=7.2Hz), 2.69(t, 2H, J=7.2Hz), 2.35(br, 4H), 1.52(m, 4H), 1.41(m, 2H), 1.34(s, 9H); MS(ESI) m/z for $C_{30}H_{35}N_3O$(MH$^+$): 454.3. |
| 3c | δ 7.82(m, 1H), 7.63(m, 1H), 7.53(m, 1H), 7.50(d, 1H, J=8.7Hz), 7.45(m, 1H), 7.40 (d, 1H, J=8.7Hz), 7.32(m, 2H), 7.17(m, 1H), 7.14(d, 1H, J=2.8Hz), 6.90(dd, 1H, J=2.8, 8.7Hz), 4.35(t, 2H, J=7.2Hz), 2.70(t, 2H, J=7.2Hz), 2.32(br, 4H), 1.49(m, 4H), 1.39(m, 2H); MS(ESI) m/z for $C_{26}H_{25}Cl_2N_3O$(MH$^+$): 466.1. |
| 3d | δ 7.64(m, 1H), 7.39(m, 5H), 7.25(m, 2H), 7.20(m, 6H), 6.89(s, 1H), 4.05(t, 2H, J=7.2Hz), 2.52(t, 2H, J=7.2Hz), 2.37(br, 4H), 1.53(m, 4H), 1.41(m, 2H); MS(ESI) m/z for $C_{28}H_{29}N_3$ (MH$^+$): 408.2. |
| 3e | δ 7.80(m, 1H), 7.53(m, 1H), 7.47(d, 1H, J=7.9Hz), 7.42(m, 2H), 7.36(m, 2H), 7.28 (m, 2H), 7.14(m, 2H), 7.05(m, 2H), 4.33(t, 2H, J=7.2Hz), 2.67(t, 2H, J=7.2Hz), 2.32(br, 4H), 1.49(m, 4H), 1.39(m, 2H); MS(ESI) m/z for $C_{26}H_{27}N_3O$(MH$^+$): 398.2. |
| 3f | δ 7.81(m, 1H), 7.64(m, 1H), 7.54(m, 2H), 7.44(m, 2H), 7.37(d, 1H, J=7.6Hz), 7.31 (m, 3H), 7.18(m, 2H), 4.35(t, 2H, J=7.2Hz), 2.70(t, 2H, J=7.2Hz), 2.31(br, 4H), 1.48(m, 4H), 1.38(m, 2H); MS(ESI) m/z for C27H26F3N3O(MH+): 466.2 |
| 3g | δ 8.54(d, 1H, J=1.6Hz), 8.14(d, 1H, J=8.0Hz), 7.91(dd, 1H, J=1.6, 8.4Hz), 7.85(m, 1H), 7.53(d, 1H, J=8.0Hz), 7.50(m, 3H), 7.31(m, 3H), 4.45(m, 4H), 2.82(t, 2H, |

TABLE 2-continued

PROTON NMR DATA AND MASS SPECTROSCOPY DATA FOR BENZIMIDAZOLE COMPOUNDS OF THE INVENTION

| Compound | $^1$H NMR(400 MHz, CDCl$_3$); MS (ESI) m/z |
|---|---|
|    | J=7.2Hz), 2.42(br, 4H), 1.59(m, 4H), 1.54(m, 2H), 1.50(t, 3H, J=7.2Hz); MS(ESI) m/z C$_{28}$H$_{30}$N$_4$ (MH$^+$): 423.2. |
| 3h | δ 7.83(m, 1H), 7.4(m, 8H), 7.31(m, 3H), 7.12(m, 1H), 5.16(s, 2H), 4.34(t, 2H, J=7.2Hz), 2.69(t, 2H, J=7.2Hz), 2.34(br, 4H), 1.51(m, 4H), 1.40(m, 2H); MS(ESI) m/z for C$_{27}$H$_{29}$N$_3$O(MH$^+$) 412.2. |
| 3i | δ 7.83(m, 1H), 7.79(d, 2H, J=8.7Hz), 7.44(m, 1H), 7.30(m, 2H), 7.08(m, 6H), 4.35 (t, 2H, J=7.2Hz), 2.73(t, 2H, J=7.2Hz), 2.38(br, 4H), 1.53(m, 4H), 1.42(m, 2H); MS (ESI) m/z for C$_{26}$H$_{26}$FN$_3$O(MH$^+$): 416.2. |

Compounds of the present invention were assayed in the electrophysiological assay discussed above. The K$_i$ values obtained from the electrophysiological assays compounds 3a–3i ranged from 180–1790 nM. The K$_i$ values for these compounds demonstrate that the compounds of the invention are potent blockers of the sodium channel.

EXAMPLE 2

Tablet Preparation

Tablets containing 25.0, 50.0, and 100.0 mg, respectively, of the compound of the invention ("active compound") are prepared as illustrated below:

| TABLET FOR DOSES CONTAINING FROM 25–100 MG OF THE ACTIVE COMPOUND | | | |
|---|---|---|---|
|  | Amount-mg | | |
| Active compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 3

Intravenous Solution Preparation

An intravenous dosage form of the compound of the invention ("active compound") is prepared as follows:

| Active compound | 0.5–10.0 mg |
|---|---|
| Sodium citrate | 5–50 mg |
| Citric acid | 1–15 mg |
| Sodium chloride | 1–8 mg |
| Water for injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having the Formula I:

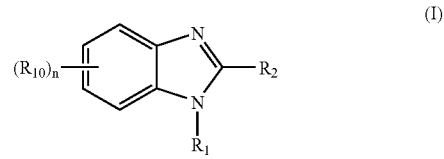

or a pharmaceutically acceptable salt, or solvate thereof, wherein:

R$_1$ is selected from the group consisting of:

where

Y is an optionally substituted C$_{2-6}$ alkylene, and

R$_3$ and R$_4$ together with the nitrogen to which they are attached form a ring having 4 or 5 carbon atoms, which ring optionally contains 1 or 2 additional heteroatoms independently selected from oxygen and NR$_5$, where R$_5$ is hydrogen or alkyl, or said ring is optionally substituted with an alkyl or aryl moiety; and (ii) piperidin-4-ylalkyl, optionally substituted by alkyl, aryl or aralkyl;

$R_2$ is selected from the group consisting of:
 (i) optionally substituted phenoxyphenyl;
 (ii) optionally substituted benzyloxyphenyl;
 (iii) optionally substituted phenylthiophenyl;
 (iv) optionally substituted benzylthiophenyl;
 (v) optionally substituted phenylaminophenyl;
 (vi) optionally substituted benzylaminophenyl;

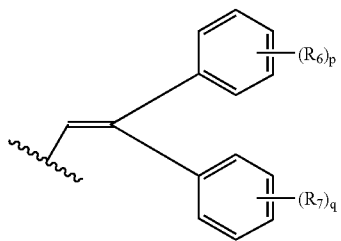
(vii)

wherein $R_6$ and $R_7$ are independently halogen, alkyl, alkoxy or haloalkyl; and p and q are integers from 0 to 4;

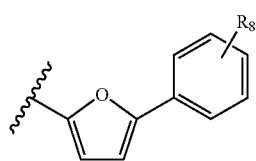
(viii)

wherein $R_8$ is hydrogen, halogen, alkyl or alkoxy;

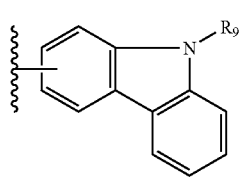
(ix)

wherein $R_9$ is hydrogen or alkyl; and
 (x) naphthalyl;
$R_{10}$ is selected from halogen, hydroxy, alkyl, alkoxy and alkoxyalkyl, wherein any alkyl moiety of $R_{10}$ can be optionally substituted by one or more of halogen or hydroxy; and
n is an integer from 0 to 4, where when n is 0, $R_{10}$ is absent and the benzene ring of the benzimidazole compound has four hydrogen atoms attached thereto, and when $R_{10}$ is present, $R_{10}$ replaces one or more of the available hydrogen atoms on the benzene ring of the benzimidazole compound.

2. The compound according to claim 1, wherein $R_1$ is —Y—$NR_3R_4$ and Y is ethylene or propylene.

3. The compound according to claim 1, wherein:
$R_2$ is optionally substituted phenoxyphenyl or optionally substituted benzyloxyphenyl; $R_1$ is —Y—$NR_3R_4$; $R_3$ and $R_4$ together with the nitrogen to which they are attached form a ring having 4 or 5 carbon atoms; and Y is an optionally substituted $C_{2-6}$ alkylene chain.

4. The compound according to claim 3, wherein $R_3$ and $R_4$ together with the nitrogen to which they are attached form a ring having 5 carbon atoms; and $R_1$ is —Y—$NR_3R_4$; wherein Y is an optionally substituted $C_{2-6}$ alkylene chain.

5. The compound according to claim 3, wherein $R_3$ and $R_4$ together with the nitrogen to which they are attached form a ring having 4 carbon atoms; and $R_1$ is —Y—$NR_3R_4$; wherein Y is an optionally substituted $C_{2-6}$ alkylene chain.

6. The compound according to claim 5, wherein $R_1$ is 2-piperidin-1-ylethyl.

7. The compound according to claim 1, wherein:
$R_2$ is optionally substituted phenoxyphenyl or optionally substituted benzyloxyphenyl; $R_1$ is —Y—$NR_3R_4$; and Y is an optionally substituted $C_{2-6}$ alkylene chain.

8. The compound according to claim 1, wherein $R_2$ is an optionally substituted phenoxyphenyl.

9. The compound according to claim 1, wherein $R_2$ is an optionally substituted benzyloxyphenyl.

10. The compound according to claim 1, wherein when $R_2$ is phenoxyphenyl or benzyloxyphenyl, and $R_2$ is attached to benzimidazole at the 3- or 4-position of the phenyl component of the phenoxyphenyl or the benzyloxyphenyl.

11. The compound according to claim 9, wherein $R_1$ is —Y—$NR_3R_4$; Y is an optionally substituted $C_{2-6}$ alkylene and $R_3$ and $R_4$ together with the nitrogen to which they are attached form a ring having 4 or 5 carbon atoms.

12. The compound according to claim 10, wherein $R_1$ is —Y—$NR_3R_4$; Y is an optionally substituted $C_{2-6}$ alkylene and $R_3$ and $R_4$ together with the nitrogen to which they are attached form a ring having 4 or 5 carbon atoms.

13. The compound according to claim 1, wherein $R_2$ is

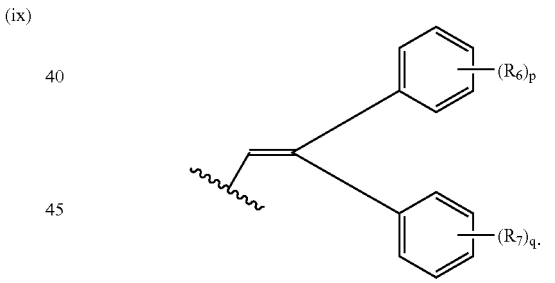

14. The compound according to claim 13, wherein $R_1$ is

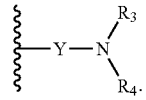

15. The compound according to claim 14, wherein Y is an optionally substituted $C_{2-6}$ alkylene, and $R_3$ and $R_4$ together with the nitrogen to which they are attached form a ring having 4 to 5 carbon atoms, which is optionally substituted with an alkyl or aryl moiety.

16. The compound according to claim 15, wherein said ring optionally contains 1 or 2 additional heteroatoms independently selected from oxygen and $NR_5$, where $R_5$ is hydrogen or alkyl.

17. The compound according to claim 1, wherein $R_2$ is

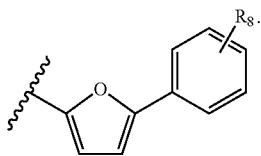

18. The compound according to claim 17, wherein $R_1$ is

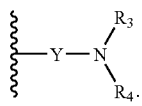

19. The compound according to claim 18, wherein Y is an optionally substituted $C_{2-6}$ alkylene, and $R_3$ and $R_4$ together with the nitrogen to which they are attached form a ring having 4 to 5 carbon atoms, which is optionally substituted with an alkyl or aryl moiety.

20. The compound according to claim 19, wherein said ring optionally contains 1 or 2 additional heteroatoms independently selected from oxygen and $NR_5$, where $R_5$ is hydrogen or alkyl.

21. The compound according to claim 1, wherein $R_2$ is

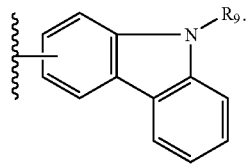

22. The compound according to claim 21, wherein $R_1$ is

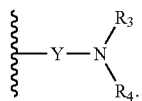

23. The compound according to claim 22, wherein Y is an optionally substituted $C_{2-6}$ alkylene, and $R_3$ and $R_4$ together with the nitrogen to which they are attached form a ring having 4 to 5 carbon atoms, optionally substituted with an alkyl or aryl moiety.

24. The compound according to claim 23, wherein said ring optionally contains 1 or 2 additional heteroatoms independently selected from oxygen and $NR_5$, where $R_5$ is hydrogen or alkyl.

25. The compound according to claim 1, wherein $R_2$ is naphthalyl.

26. The compound according to claim 25, wherein $R_1$ is

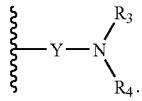

27. The compound according to claim 25, wherein Y is an optionally substituted $C_{2-6}$ alkylene, and $R_3$ and $R_4$ together with the nitrogen to which they are attached form a ring having 4 to 5 carbon atoms, which is optionally substituted with an alkyl or aryl moiety.

28. The compound according to claim 27, wherein said ring optionally contains 1 or 2 additional heteroatoms independently selected from oxygen and $NR_5$, where $R_5$ is hydrogen or alkyl.

29. The compound according to claim 1, wherein said compound is selected from the group consisting of:

3-(2-piperidinylethyl)-2-(4-phenoxyphenyl) benzimidazole;

3-(2-piperidinylethyl)-2-(3-(4-tert-butylphenoxy)phenyl) benzimidazole;

3-(2-piperidinylethyl)-2-(3-(3,4-dichlorophenoxy)phenyl) benzimidazole;

3-(2-piperidinylethyl)-2-(2,2-diphenylethenyl) benzimidazole;

3-(2-piperidinylethyl)-2-(3-phenoxyphenyl) benzimidazole;

3-(2-piperidinylethyl)-2-(3-(3-trifluromethylphenoxy) phenyl) benzimidazole;

3-(2-piperidinylethyl)-2-(N-ethyl-3-carbazolyl) benzimidazole;

3-(2-piperidinylethyl)-2-(3-benzyloxyphenyl) benzimidazole; and 3-(2-piperidinylethyl)-2-(4-(4-fluorophenoxy)phenyl) benzimidazole.

30. A pharmaceutical composition, comprising the compound of claim 1 and a pharmaceutically acceptable carrier or diluent.

31. A method of making a compound according to claim 1 wherein said method comprises:
(a) reacting a primary amine with 2-fluoro-1-nitrobenzene to produce an amine substituted nitrobenzene;
(b) reducing said amine substituted nitrobenzene obtained in (a) in the presence of hydrogen and a catalyst to produce an amine substituted aniline; and
(c) reacting said amine substituted aniline obtained in step (b), with an aldehyde to produce a substituted benzimidazole of Formula I.

32. The method according to claim 31, wherein said catalyst is a metal catalyst.

33. The method according to claim 32, wherein said metal catalyst comprises a metal selected from the group consisting of: Zn, Sn, Fe, Al, Ti and Pd.

34. The method according to claim 33, wherein said metal catalyst is Pd/C.

35. The method according to claim 31, wherein the reactions of steps (a) and (b) are carried out for about 14 to about 17 hours.

36. The method according to claim 31, wherein the reaction of step (c) is carried out for about 45 to about 50 hours.

37. The method according to claim 31, wherein step (b) is carried out in the presence of methanol.

38. The method according to claim 31, wherein step (c) is carried out in the presence of nitrobenzene and a temperature of about 100° C.

39. The method according to claim 31, wherein said primary amine of step (a) is selected from the group consisting of:

(i) an amine of the formula:

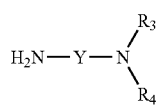

wherein

Y is an optionally substituted $C_{2-6}$ alkylene; and $R_3$ and $R_4$ together with the nitrogen to which they are attached form a ring having 4 or 5 carbons, which ring optionally contains 1 or 2 additional heteroatoms independently selected from oxygen and $NR_5$, where $R_5$ is hydrogen or alkyl, or said ring is optionally substituted with an alkyl or aryl moiety; and (ii) an optionally substituted piperidin-4-ylalkyl amine, wherein optional substituents are selected from the group consisting of alkyl, aryl and aralkyl.

40. The method according to claim 31, wherein said aldehyde of step (c) has the formula:

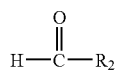

wherein:

$R_2$ is selected from the group consisting of:

(i) optionally substituted phenoxyphenyl;
(ii) optionally substituted benzyloxyphenyl;
(iii) optionally substituted phenylthiophenyl;
(iv) optionally substituted benzylthiophenyl;
(v) optionally substituted phenylaminophenyl;
(vi) optionally substituted benzylaminophenyl;

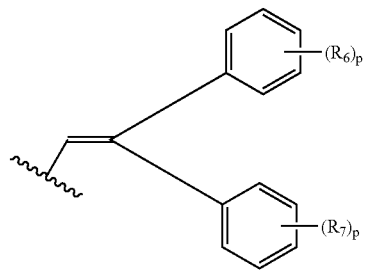

wherein $R_6$ and $R_7$ are independently halogen, alkyl, alkoxy or haloalkyl; and p and q are integers from 0 to 4;

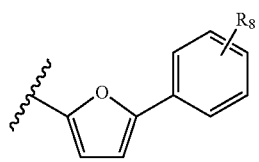

wherein $R_8$ is hydrogen, halogen, alkyl or alkoxy;

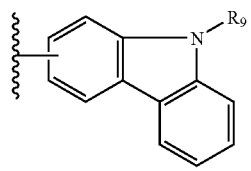

wherein $R_9$ is hydrogen or alkyl; and (x) naphthalyl.

41. The method according to claim 39, wherein said primary amine is 1-(2-aminoethyl) piperidine.

42. A pharmaceutical composition comprising an effective amount of the compound according to claim 1, or a pharmaceutically acceptable salt thereof, and a pharmaceutically acceptable carrier.

43. The compound according to claim 1, wherein n is 0.

* * * * *